United States Patent
Faict et al.

[11] Patent Number: 5,881,879
[45] Date of Patent: *Mar. 16, 1999

[54] SYSTEM FOR PRESERVING AND DELIVERING GAS-CONTAINING SOLUTIONS

[75] Inventors: Dirk Faict, Assenede; Anne Leyssens, Hasselt; Annick Duponchelle, Brussels; Jean-Pierre Hartman, Sint Genesius Rode, all of Belgium

[73] Assignee: Baxter International Inc., Deerfield, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 798,399

[22] Filed: Feb. 7, 1997

[51] Int. Cl.$^6$ .................................................. B65D 85/00
[52] U.S. Cl. ........................ 206/459.1; 206/438; 206/807; 422/58
[58] Field of Search .................... 206/438, 459.1, 206/807; 422/55, 58, 119, 83, 86

[56] References Cited

U.S. PATENT DOCUMENTS

| | | | |
|---|---|---|---|
| 5,064,664 | 11/1991 | Hustad | 206/459.1 |
| 5,124,129 | 6/1992 | Riccitelli et al. | |
| 5,156,159 | 10/1992 | Lampotang et al. | |
| 5,344,017 | 9/1994 | Wittrock | 206/459.1 |
| 5,375,592 | 12/1994 | Kirk et al. | |
| 5,578,023 | 11/1996 | Schneider | 206/459.1 |
| 5,617,812 | 4/1997 | Balderson et al. | 206/459.1 |
| 5,620,656 | 4/1997 | Wensky et al. | 206/459.1 |
| 5,644,899 | 7/1997 | Trusedale | 206/459.1 |

FOREIGN PATENT DOCUMENTS

| | | |
|---|---|---|
| 0 121 831 A2 | 3/1984 | European Pat. Off. |
| WO 90/01695 | 2/1990 | WIPO |
| 9315402 | 8/1993 | WIPO |
| WO 93/20431 | 12/1993 | WIPO |
| WO 94/00756 | 1/1994 | WIPO |
| 9425084 | 11/1994 | WIPO |
| WO 95/16052 | 6/1995 | WIPO |
| WO 95/22759 | 8/1995 | WIPO |
| 9748365 | 12/1997 | WIPO |

Primary Examiner—Paul T. Sewell
Assistant Examiner—Nhan T. Lam
Attorney, Agent, or Firm—Thomas S. Borecki; Charles R. Mattenson; Robert M. Barrett

[57] ABSTRACT

A container system for containing and preserving gas generating solutions such as bicarbonate-containing solutions is provided. The system includes an outer container or barrier that is gas impermeable. The system also includes an indicator for visually indicating when gas has been permitted to leak or escape from the outer container thereby changing the physical characteristics of the gas generating solution.

19 Claims, 3 Drawing Sheets

SYSTEM FOR PRESERVING AND DELIVERING GAS-CONTAINING SOLUTIONS

BACKGROUND OF THE INVENTION

The present invention relates generally to a system and a method for containing and preserving gas containing solutions, such as bicarbonate containing solutions, for future delivery or use. More specifically, the present invention relates to a system for containing a gas containing solution that provides a visual indication in the event gas leaks from the container system.

Gas containing solutions, such as bicarbonate-containing solutions, are often used in medical procedures. Specifically, bicarbonate-containing solutions are often used for hemodialysis or peritoneal dialysis solutions. In a bicarbonate-containing solution, bicarbonate is in equilibrium with carbon dioxide. Because carbon dioxide is a gas at room temperature and atmospheric pressure, the carbon dioxide easily escapes from the solution. The escape of carbon dioxide from the solution needs to be avoided because it changes the physical and chemical characteristics of the solution. For example, the release of carbon dioxide from a bicarbonate-containing solution will increase the pH of the solution. Of course, any change in the characteristics of the bicarbonate-containing solution is undesirable when the solution is being used for medical purposes.

Therefore, the release of carbon dioxide from a bicarbonate-containing solution that is to be used for medical purposes, such as a dialysis solution, needs to be avoided. Further, for other gas-containing solutions in which a gas is in equilibrium with a solute, the release of the gas from the container, vessel or package containing the solution needs to be avoided because, as discussed above, the release of the gas will change the characteristics of the solution.

Until now, attempts at preventing the release of gas from a solution container have been directed toward obtaining fail-proof container designs. For example, gas impermeable materials have been used which prevent carbon dioxide or other gases from escaping the container to ensure the stability of the solution. However, the accidental damage of the gas impermeable material always remains a possibility. Further, in the case of bicarbonate-containing solutions, carbon dioxide is a colorless and odorless gas. Therefore, any leakage of carbon dioxide from the container will go undetected by the user.

Accordingly, there is a need for an improved container system for containing and preserving gas containing solutions such as bicarbonate-containing solutions which will provide a visual indication to the user in the event the gas barrier capabilities of the container system have been impaired or compromised. With such an improved container system, medical personnel or patients utilizing bicarbonate-containing dialysis solutions will be provided with a visual indicator in the event carbon dioxide has been permitted to leak or escape from the container system resulting in a change to the characteristics of the dialysis solution. Further, users of other gas containing solutions will be provided with a visual indicator in the event gas has been permitted to leak from the containment system thereby altering the physical and/or chemical characteristics of the solution.

SUMMARY OF THE INVENTION

The present invention provides a container system for a gas containing solution and a method for containing a gas containing solution. The container system of the present invention provides a visual indication to the user of the system in the event gas has been permitted to leak or escape from the system.

To this end, in an embodiment, a system is provided for packaging a gas containing solution. In an embodiment, the system includes a gas impermeable container that houses the solution and an indicator device for indicating a change in one or more physical and/or chemical characteristics of the solution which would result in the event gas is permitted to leak or escape from the container.

In an embodiment, the system has an inner gas permeable container disposed within an outer gas impermeable container. The inner gas permeable container is at least partially filled with the gas containing solution. The gas is contained between the inner and outer containers because of the gas impermeable properties of the outer container. An indicator is provided either between the inner and outer containers or within the inner container which indicates a change in one or more physical and/or chemical characteristics of the solution in the event gas is permitted to leak or escape from the system.

In an embodiment, a space is provided between the inner and outer container which serves to contain gas generated by the solution and passed through the walls of the inner container.

In an embodiment, a system is provided for containing and preserving a bicarbonate-containing solution. A gas permeable inner container contains the bicarbonate solution. The inner container is disposed within a larger gas impermeable outer container. The gas generated by the bicarbonate-containing solution is contained within a space provided between the inner and outer containers. An indicator is disposed within the outer container for providing a visual indication to the user when carbon dioxide gas has been permitted to leak through or escape from the outer container.

In an embodiment, the indicator is disposed between the inner and outer containers.

In an embodiment, the indicator is disposed within the inner container.

In an embodiment, the indicator device is provided in a tablet form, consisting of a binder and an indicator substance.

In an embodiment, the indicator device comprises a container made of a gas permeable material containing an indicator substance.

In an embodiment, the indicator device comprises a container made of a gas permeable material containing a solution and an indicator substance.

In an embodiment, the indicator device comprises a tablet, consisting of powder and an indicator substance, with or without alkalizing or acidifying agents.

In an embodiment, the indicator device comprises a container made of a gas permeable material containing a powder and an indicator substance.

In an embodiment, the indicator device comprises an indicator substance as well as moisturizing agents, electrolytes and/or stabilizers.

In an embodiment, the indicator substance is a substance that changes characteristics, for example, color when the pH of its surroundings changes.

In an embodiment, the indicator substance is cresol red (o-cresolsulfonephthalein).

In an embodiment, the indicator substance is m-cresol purple (m-cresolsulfonephthalein).

In an embodiment, the indicator substance is α-napthtolazobenzene-p-sulfonic acid.

In an embodiment, the indicator substance is thymol blue (thymolsulfonephtalein).

In an embodiment, the indicator substance is bromothymol blue (dibromothymolsulfonephtalein).

In an embodiment, the indicator substance is p-xylenolsulfonephtalein.

In an embodiment, the indicator substance is phenol red (phenolsulfonephthalein).

In an embodiment, the inner gas permeable container can be a multiple chambered container with one or more compartments filled with the bicarbonate-containing solution or the gas-containing solution.

In an embodiment, the present invention provides a method for containing a gas containing solution. The method comprises the steps of filling a gas permeable inner container with the gas containing solution, sealing the inner container, enclosing the inner container within a larger gas impermeable outer container thereby leaving a space disposed between the inner and outer containers for containing a quantity of gas generated by the solution and passed through the walls of the inner container, placing an indicator between the inner and outer containers for indicating a change in at least one physical and/or chemical characteristic of the gas containing solution and, sealing the outer container.

In an embodiment, the indicator is disposed within the gas permeable inner container as opposed to the space between the inner and outer containers.

It is, therefore, an advantage of the present invention to provide an improved container system for containing and preserving bicarbonate-containing solutions.

Another advantage of the present invention is an improved container system for containing and preserving gas generating or containing solutions.

Another advantage of the present invention is an improved container system for containing and preserving bicarbonate-containing solutions which further provides a visual indication to the user in the event carbon dioxide has leaked from or escaped from the system.

Yet another advantage of the present invention is to provide an improved system for containing and preserving gas generating or containing solutions which provides a visual indication to the user in the event gas has been permitted to leak from or escape from the system.

A still further advantage of the present invention is to provide an improved system and a method for the containment and preservation of gas generating or containing solutions which provides the user with a visual indication in the event the gas barrier characteristics of the system have been impaired or compromised.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a system and a method for containing and preserving gas-generating solutions such as bicarbonate-containing solutions. More specifically, the present invention provides a system and a method for containing gas containing solutions, including bicarbonate-containing solutions, which provides a visual indication to the user in the event gas is permitted to leak or escape from the system.

Figure 1:
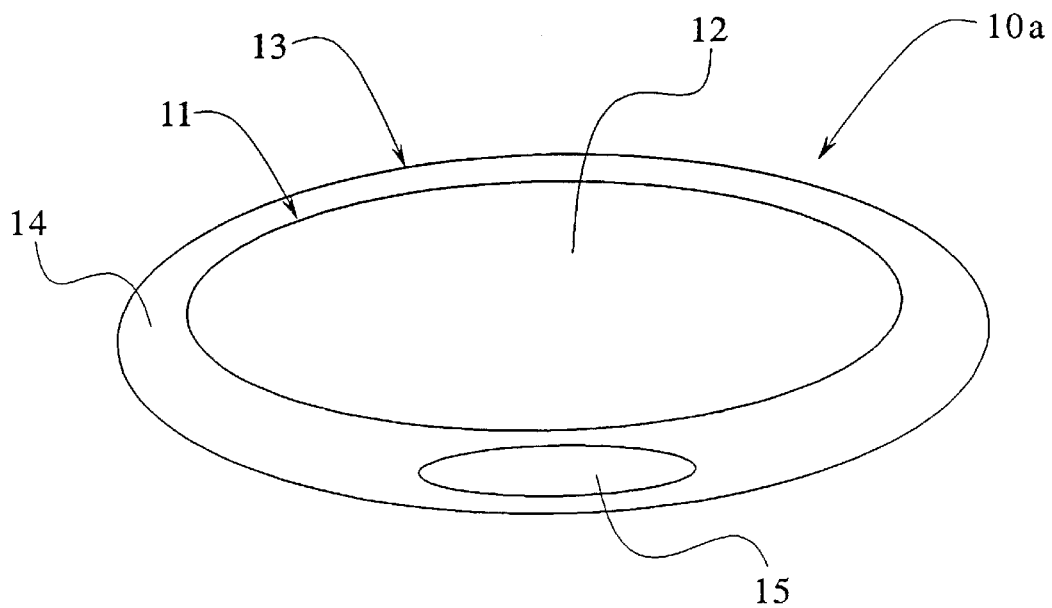
FIG. 1 illustrates, schematically, an embodiment of a container system of the present invention.

As illustrated in FIG. 1, the system 10a of the present invention includes an inner container 11 which is at least partially filled with the gas generating solution shown at 12. The inner container 11 and solution 12 are housed within an outer container 13. The inner container 11 is made from a gas permeable material; the outer container 13 is made from a gas impermeable material. The outer container 13 is larger than the inner container 11 thereby providing a space shown at 14 between the inner container 11 and the outer container 13. The space 14 contains gas that is generated by the solution 12 that passes through the walls of the inner container 11 but which is not permitted to pass through the gas impermeable outer container 13.

However, in the event the outer container 13 becomes damaged or otherwise impaired, gas may leak from the outer container 13 to the atmosphere. In such a situation, an indicator 15 is provided which will detect a change in condition within the space 14. Specifically, in the case where the solution 12 is bicarbonate-containing solution, the space 14 is at least partially filled with carbon dioxide. If the carbon dioxide is permitted to escape through the outer container 13, the partial pressure of carbon dioxide within the space 14 will decrease as the carbon dioxide escapes from the space 14 and air enters the space 14. The indicator 15 will provide a visual indication of this lowering of the carbon dioxide partial pressure. Preferably, the indicator 15 will change color as the partial pressure of carbon dioxide decreases and air enters the space 14.

Figure 2:
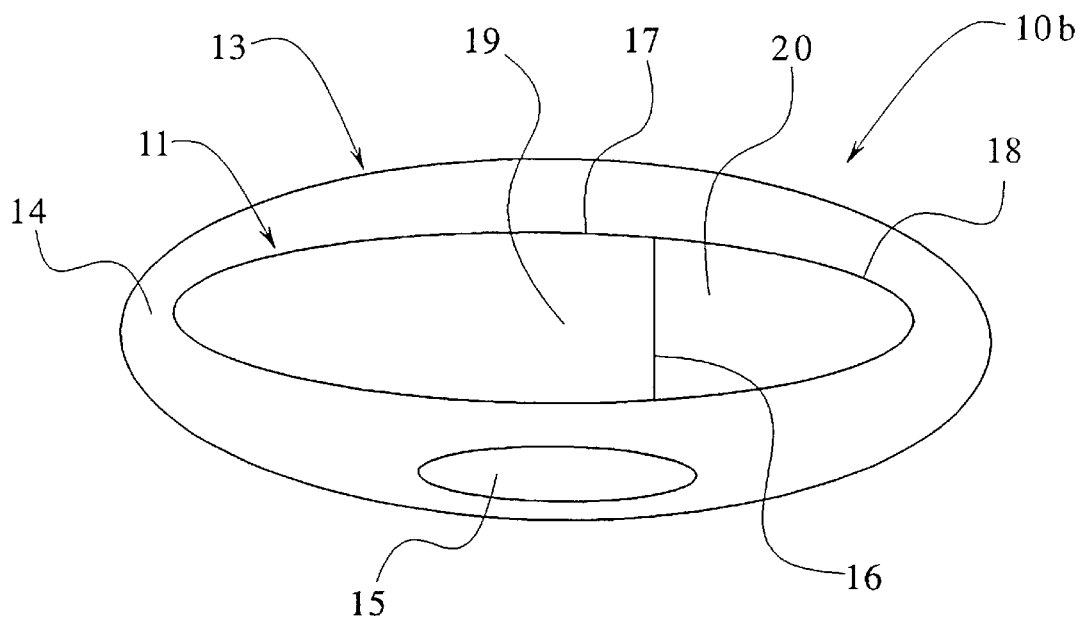
FIG. 2 illustrates, schematically, an embodiment of a container system of the present invention.

As illustrated in FIG. 2, the system 10b is equipped with an inner container 11 that includes a separating wall 16 that divides the container 11 into two separate compartments 17, 18. The compartments 17, 18 contain isolated solutions 19, 20 respectively. Again, the indicator 15 is provided to detect the change in partial pressure of gas disposed within the space 14 in the event the gas barrier properties of the outer container 13 become impaired or compromised. The isolated solutions 19, 20 may be used separately so that two solutions 19, 20 may be housed within one system 10b that provides a visual indication in the event the gas barrier properties of the outer container 13 become impaired or compromised. Further, in some applications, the bicarbonate solution is a ready-to-use medical solution. In contrast, the bicarbonate solutions that are used for peritoneal dialysis are typically provided in bags having two separated chambers. One chamber contains a solution of dextrose and calcium, the other chamber contains the solution of bicarbonate and carbon dioxide gas. These substances cannot be sterilized by heat together and are therefore separated. Both chambers are connected by a frangible or peel seal to allow sterile reconstitution before use. For these applications, the container system 10b as illustrated in FIG. 2 is particularly appropriate. Further, by providing two solutions 19, 20 in one system 10b, the packaging cost per solution is decreased and sterile reconstitution is favored in case this is needed.

Figure 3:
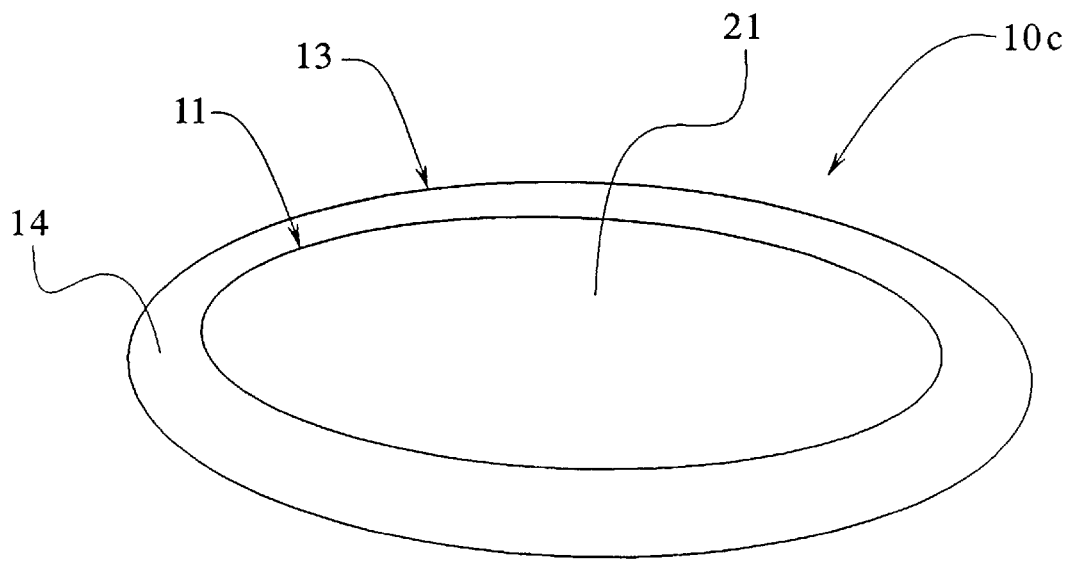
FIG. 3 illustrates, schematically, an embodiment of a container system of the present invention.
Figure 4:
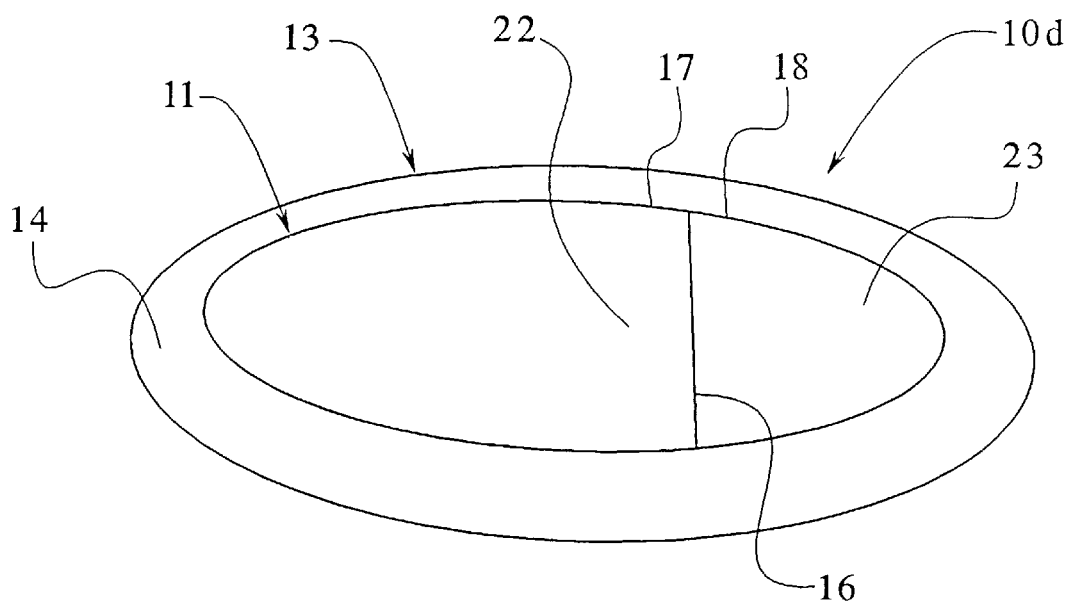
FIG. 4 illustrates, schematically, an embodiment of a container system of the present invention.

The systems 10c and 10d as illustrated in FIGS. 3 and 4 do not include an indicator 15 disposed between the inner container 11 and outer container 13 as illustrated in FIGS. 1 and 2. In contrast, the solution 21 (FIG. 3) contains an indicator dissolved within the solution 21. In the event the solution 21 is a bicarbonate-containing solution and the outer container 13 leaks or permits carbon dioxide to pass through the outer container 13, the pH of the solution 21 will increase. As a result, the indicator dissolved within the solution 21 will change color thereby providing a visual indication to the user that the physical characteristics of the solution 21 have been changed and that the solution 21 should not be used.

In the event that it is undesirable to dissolve an indicator within a solution that is to be used by a patient, the inner container 11 can be divided into one or more walls 16 so that the inner container 11 is divided into two or more compartments 17, 18. Then, an indicator may be dissolved in either the solution 22 or the solution 23 illustrated in FIG. 4. Preferably, the solution contained within the smaller compartment, or the solution 23 contained within the smaller compartment 18 will include the dissolved indicator. If the outer container has leaked, the smaller solution 23 containing the dissolved indicator will have changed color alerting the patient not to use the solution 22 or any of the solutions contained within the system 10d and that the system 10d should be simply discarded.

Figure 5:
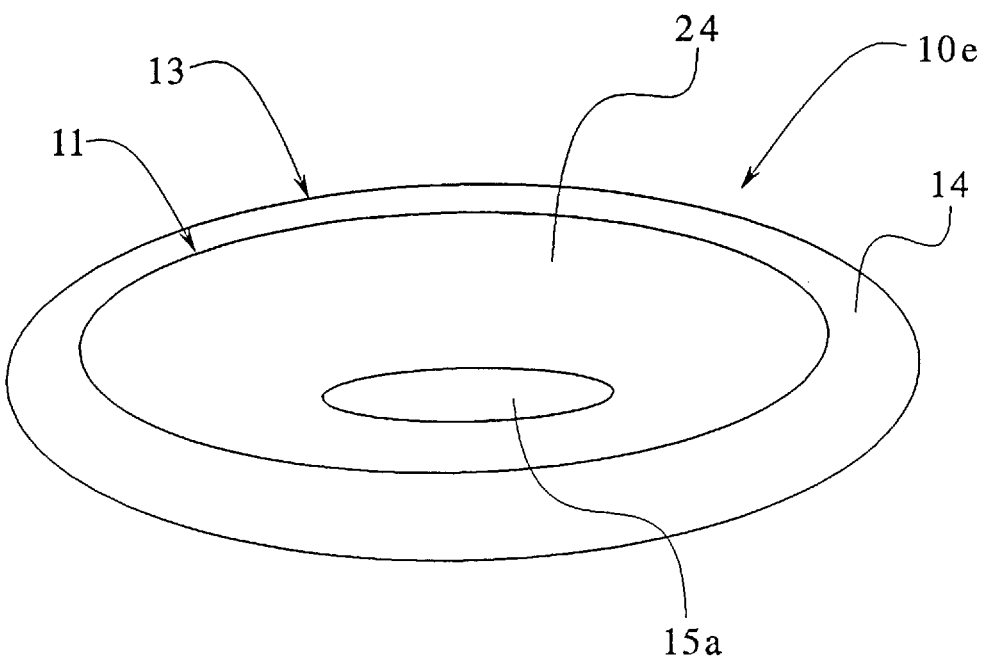
FIG. 5 illustrates, schematically, an embodiment of a container system of the present invention.

FIG. 5 illustrates a container 10e which features an inner gas permeable container 11 disposed within an outer gas impermeable container 13. An indicator 15a is disposed within the bicarbonate containing solution 24. The housing of the indicator 15a is gas permeable. Hence, if carbon dioxide gas is permitted to leak through the inner container 11 and out through the outer container 13, the concentration of the carbon dioxide exposed to the indicator 15a will change and, hence, the indicator 15a can change color or otherwise provide a visual indication that carbon dioxide, or any gas contained within the solution 24 for that matter, has been permitted to leak from the system 10e.

Figure 6:
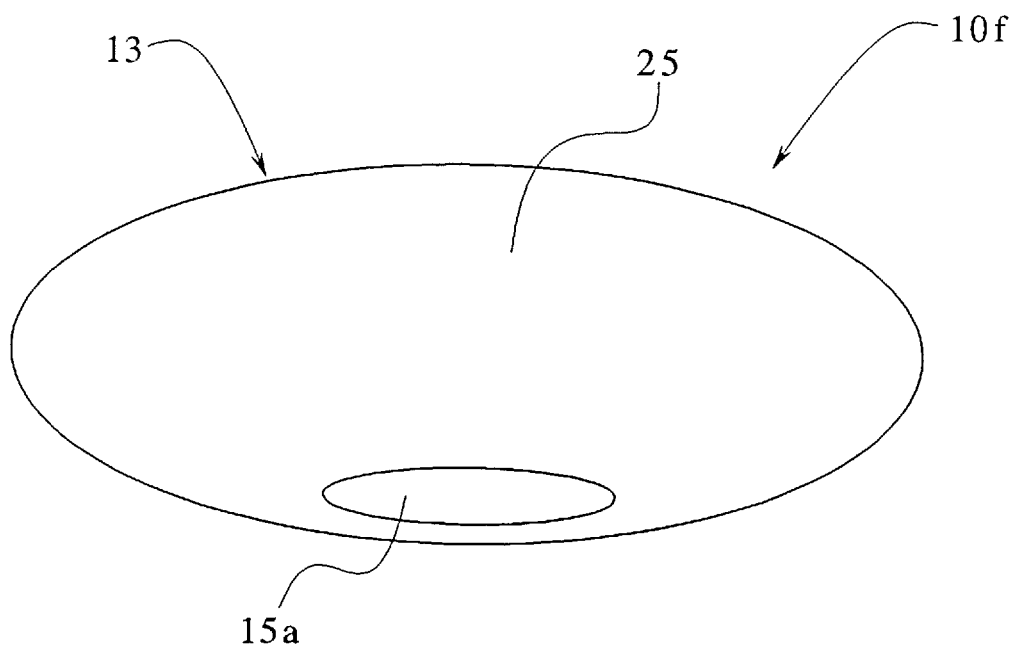
FIG. 6 illustrates, schematically, an embodiment of a container system of the present invention.

FIG. 6 illustrates a system 10e which includes only an outer impermeable container 13 that houses a solution 25. An indicator 15a is disposed within the solution 25 and the housing of the indicator 15a is gas permeable. If gas is permitted to leak from the outer container 13, the concentration of gas exposed to the indicator 15a will change and, hence, the indicator 15a can provide a visual indication of this change to the user.

The system of the present invention is especially useful for containing bicarbonate-containing dialysis solutions. A visual indication, by way of an indicator 15 disposed between the inner container 11 and outer container 13 or, in contrast, a dissolved indicator in the bicarbonate-containing solution 21 (FIG. 3) or one of the bicarbonate-containing solutions 23 (FIG. 4) or floating indicator provide the patient with a visual indication when the gas barrier properties of the outer container 13 have failed or have been compromised. Thus, the patient or medical technician is provided with a visual indication that the properties of the solution have changed and that the product should be discarded. Of course, the system of the present invention is applicable to other gas containing or generating solutions in addition to bicarbonate-containing solutions.

The substances available for use as an indicator include, but are not limited to cresol red (o-cresolsulfonephthalein), m-cresol purple (m-cresolsulfonephthalein), α-napthtolazobenzene-p-sulfonic acid, thymol blue (thymolsulfonephtalein), bromothymol blue (dibromothymolsulfonephtalein), p-xylenolsulfonephtalein and phenol red (phenolsulfonephthalein) or combinations.

The outer container 13 is preferably fabricated from a gas impermeable material, such as a multi-layer laminated or co-extruded material which contains a gas barrier element such as aluminum, polyamide, ethylene vinyl alcohol, polyvinylidene chloride, and/or an intermediate layer with aluminum oxide or silicon oxide deposit coating. An appropriate mono-layer of these materials will also work. In the alternative, a thick permeable material such as polyvinyl chloride can be used since a thick layer of such material will reduce the permeability to an appropriate level.

The inner container 11 is preferably fabricated from a gas permeable material such as polyvinyl chloride or polypropylene obtained by blow molding and/or extruding or a mono-layer or a multi-layer of laminated or co-extruded polyolefin-based material.

The materials for the outer container 13 and the inner container 11 should, of course, be selected so that the inner container 11 is relatively gas permeable, whereas the outer container 13 is relatively gas impermeable. The inner container 11 should be at least twice as permeable as the outer container 13. Preferably, the inner container 11 is 10 to about 1,000 times more permeable than the outer container 13. The inner container 11 should be sufficiently permeable to allow an equilibrium to be established between the solution contained within the inner container 11 and the gas contained in the space 14 disposed between the inner container 11 and outer container 13.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

What is claimed is:

1. A container system for a gas and a gas containing and generating solution that generates the gas while said solution is contained within said container system, the container system comprising:

a gas permeable inner container enclosed within a gas impermeable outer container with a space located between at least portions of the inner and outer containers, the inner container containing a gas containing and generating solution, the space disposed between the inner and outer containers containing a partial pressure of a gas generated by the solution and which has passed through the inner container into said space, and an indicator for indicating migration of the gas through the outer container which results in a reduction in the partial pressure of the gas in the space and a change in at least one physical or chemical characteristic of the solution.

2. The container system of claim 1 wherein the indicator is enclosed in a gas permeable capsule.

3. The container system of claim 1 wherein the indicator is disposed in the space between the inner and outer containers.

4. The container system of claim 1 wherein the indicator is disposed inside the inner container.

5. The container system of claim 4 wherein the indicator comprises a gas permeable bag containing an indicator substance.

6. The container system of claim 1 wherein the gas containing and generating solution has a pH and the indicator indicates a change in the pH of the solution.

7. The container system of claim 1 wherein the indicator indicates a change in the composition of the solution.

8. The container system of claim 1 wherein the indicator comprises an indicating substance selected from the group consisting of cresol red (o-cresolsulfonephthalein), m-cresol purple (m-cresolsulfonephthalein), α-napthtolazobenzene-p-sulfonic acid, thymol blue (thymolsulfonephtalein), bromothymol blue (dibromothymolsulfonephtalein), p-xylenolsulfonephtalein and phenol red (phenolsulfonephthalein).

9. The container system of claim 1 wherein the inner container further comprises a plurality of compartments for containing gas containing or generating solutions.

10. A container system for carbon dioxide gas and a carbon dioxide containing and generating solution that generates a gas while said solution is contained within said system, the carbon dioxide containing and generating solution having a pH, the container system comprising:
 a carbon dioxide permeable inner container disposed within a carbon dioxide impermeable outer container with a space disposed between the inner and outer containers, the inner container containing a carbon dioxide containing or generating solution, the space disposed between the inner and outer containers containing a partial pressure of carbon dioxide gas generated by the carbon dioxide containing and generating solution and which has passed through the inner container,
 an indicator for indicating a change in a pH of the solution.

11. The container system of claim 10 wherein the indicator is disposed in the space between the inner and outer containers.

12. The container system of claim 10 wherein the indicator is disposed inside the inner container.

13. The container system of claim 10 wherein the indicator comprises an indicating substance selected from the group consisting of cresol red (o-cresolsulfonephthalein), m-cresol purple (m-cresolsulfonephthalein), α-napthtolazobenzene-p-sulfonic acid, thymol blue (thymolsulfonephtalein), bromothymol blue (dibromothymolsulfonephtalein), p-xylenolsulfonephtalein and phenol red (phenolsulfonephthalein).

14. The container system of claim 10 wherein the inner container further comprises a plurality of compartments for containing gas containing or generating solutions.

15. A container system for a bicarbonate solution that generates carbon dioxide gas while the solution is contained within said container system, the container system comprising:
 a carbon dioxide permeable inner container disposed within a carbon dioxide impermeable outer container with a space disposed between the inner and outer containers, the inner container containing a bicarbonate solution, the space disposed between the inner and outer containers for containing a partial pressure of carbon dioxide gas generated by the bicarbonate solution and which has passed through the inner container,
 an indicator for indicating a change in the partial pressure of carbon dioxide gas located in the space between the inner and outer containers.

16. The container system of claim 15 wherein the indicator is disposed in the space between the inner and outer containers.

17. The container system of claim 15 wherein the indicator is disposed inside the inner container.

18. The container system of claim 15 wherein the indicator comprises an indicating substance selected from the group consisting of cresol red (o-cresolsulfonephthalein), m-cresol purple (m-cresolsulfonephthalein), α-napthtolazobenzene-p-sulfonic acid, thymol blue (thymolsulfonephtalein), bromothymol blue (dibromothymolsulfonephtalein), p-xylenolsulfonephtalein and phenol red (phenolsulfonephthalein).

19. The container system of claim 15 wherein the inner container further comprises a plurality of compartments for containing bicarbonate solutions.

\* \* \* \* \*